United States Patent
Campbell

(10) Patent No.: US 11,992,657 B2
(45) Date of Patent: May 28, 2024

(54) DETECTION OF AUDIBLE ALERTS

(71) Applicant: Medtronic MiniMed, Inc., Northridge, CA (US)

(72) Inventor: Alexander S. Campbell, Encino, CA (US)

(73) Assignee: MEDTRONIC MINIMED, INC., Northridge, CA (US)

(*) Notice: Subject to any disclaimer, the term of this patent is extended or adjusted under 35 U.S.C. 154(b) by 171 days.

(21) Appl. No.: 17/165,365

(22) Filed: Feb. 2, 2021

(65) Prior Publication Data

US 2022/0241502 A1    Aug. 4, 2022

(51) Int. Cl.
*A61M 5/00* (2006.01)
*A61M 5/172* (2006.01)
*G16H 20/17* (2018.01)

(52) U.S. Cl.
CPC .......... *A61M 5/1723* (2013.01); *G16H 20/17* (2018.01); *A61M 2205/18* (2013.01); *A61M 2205/3553* (2013.01); *A61M 2205/581* (2013.01)

(58) Field of Classification Search
CPC ............ A61M 5/1723; A61M 2205/18; A61M 2205/3553; A61M 2205/581; A61M 1/16; A61M 1/28; A61M 2205/186; A61M 2205/3306; A61M 2205/3375; A61M 2205/502; A61M 2205/702; G16H 20/17; G10L 21/10; G10L 21/00; G10L 21/06; G10L 2021/105; G10L 21/12; G10L 21/14; G10L 25/60; G06F 3/167; G06F 3/0481; G06F 3/165; G06F 9/542; H04M 1/72403; H04R 3/005; H04R 3/10; H04R 2410/07; H04R 2499/11
See application file for complete search history.

(56) References Cited

U.S. PATENT DOCUMENTS

| | | | |
|---|---|---|---|
| 9,636,456 B2 | 5/2017 | Talbot et al. | |
| 9,974,903 B1 | 5/2018 | Davis et al. | |
| 2008/0300572 A1 | 12/2008 | Rankers et al. | |
| 2011/0190595 A1* | 8/2011 | Bennett | A61B 1/05 600/300 |
| 2013/0197320 A1 | 8/2013 | Albert et al. | |
| 2016/0263316 A1 | 9/2016 | Moran et al. | |
| 2017/0181645 A1 | 6/2017 | Mahalingam et al. | |
| 2018/0211551 A1 | 7/2018 | Mayou et al. | |
| 2019/0175822 A1 | 6/2019 | Kamen et al. | |
| 2019/0192764 A1 | 6/2019 | Brewer et al. | |
| 2020/0250939 A1 | 8/2020 | Mears | |

FOREIGN PATENT DOCUMENTS

| WO | WO-2008008916 A2 * | 1/2008 | ......... G06F 19/3418 |
|---|---|---|---|
| WO | WO-2015062896 A1 * | 5/2015 | ............. G06F 19/00 |
| WO | WO-2021108214 A1 * | 6/2021 | ............. A61M 1/16 |

* cited by examiner

*Primary Examiner* — James J Yang
*Assistant Examiner* — Anthony D Afrifa-Kyei
(74) *Attorney, Agent, or Firm* — Weaver Austin Villeneuve & Sampson LLP

(57) ABSTRACT

A medical device may determine an occurrence of an alert condition. The medical device may transmit, to a separate device, data indicative of the occurrence of the alert condition. After transmitting the data indicative of the occurrence of the alert condition to the separate device, the medical device may determine, based on an audio signal generated by a microphone of the medical device, that the separate device has outputted an audible alert. The audio signal may correspond to audio captured by the microphone.

18 Claims, 3 Drawing Sheets

DETECTION OF AUDIBLE ALERTS

TECHNICAL FIELD

The disclosure relates to medical systems and, more particularly, to audible alerts used with medical systems.

BACKGROUND

A patient with diabetes typically receives insulin from an insulin delivery device, such as a pump or injection device, to manage glucose levels. A sensor integrated into the insulin delivery device or separate from the insulin delivery device may measure the patient's glucose levels. The insulin delivery device may be used to control the amount of insulin that is delivered based on the measured glucose level.

SUMMARY

Disclosed herein are techniques for detecting audible alerts. The techniques may be practiced using systems; devices; processor-implemented methods; and non-transitory processor-readable storage media storing instructions which, when executed by one or more processors, cause performance of the technique.

In some embodiments, the techniques may involve determining an occurrence of an alert condition. The techniques may also involve transmitting, to a separate device, data indicative of the occurrence of the alert condition. The techniques may further involve, after transmitting the data indicative of the occurrence of the alert condition to the separate device, determining, based on an audio signal generated by a microphone, that the separate device has outputted an audible alert.

The details of one or more aspects of the disclosure are set forth in the accompanying drawings and the description below. Other features, objects, and advantages of this disclosure will be apparent from the description and drawings, and from the claims.

DETAILED DESCRIPTION

Devices, systems, and techniques for detecting audible alerts (e.g., alarms) are described in this disclosure. Although described below with respect to disposable medical devices and smartphones, the example techniques should not be considered limited to disposable medical devices and smartphones.

Increasingly, medical devices (e.g., insulin pumps, glucose sensors, and the like) are used in conjunction with a patient's smartphone or some other external controller. This trend is particularly notable in disposable medical devices (e.g., patch pumps or glucose sensors), which may not include output devices (e.g., a speaker device) for outputting alerts. Instead, to output an alert, such medical devices may communicate with the patient's smartphone or external controller to cause the patient's smartphone or external controller to output alerts (e.g., via the smartphone's speaker).

However, the patient's smartphone or external controller may, in certain circumstances, fail to output an alert that is audible to the patient. For example, the smartphone may be set to a silent mode or a "do not disturb" mode and thus fail to output an audible alert. In some examples, the smartphone may be too far away from the patient such that an alert outputted by the smartphone may not be loud enough to be clearly heard by the patient.

As such, to determine whether the patient's smartphone did in fact output an audible alert, the medical device may include a microphone for capturing audio and for generating a corresponding audio signal. The audio signal may be analyzed based on application of a Goertzel filter to determine whether a particular tone corresponding to the audible alert is present in the audio. Because application of a Goertzel filter is a computationally efficient technique for tone detection, the medical device's relatively low-powered processing circuitry can be used to quickly detect, in a power-efficient manner, whether the patient's smartphone did in fact output an audible alert.

Upon determining that the patient's smartphone failed to output an audible alert, the medical device may perform any of a variety of remedial actions. For example, the medical device may raise a backup alert or cause the patient's smartphone to output the alert at a higher volume. In some embodiments, one or more remedial action may be repeated until the microphone of the medical device detects the alert. In this way, the techniques disclosed herein may help ensure that the patient is alerted.

Figure 1:
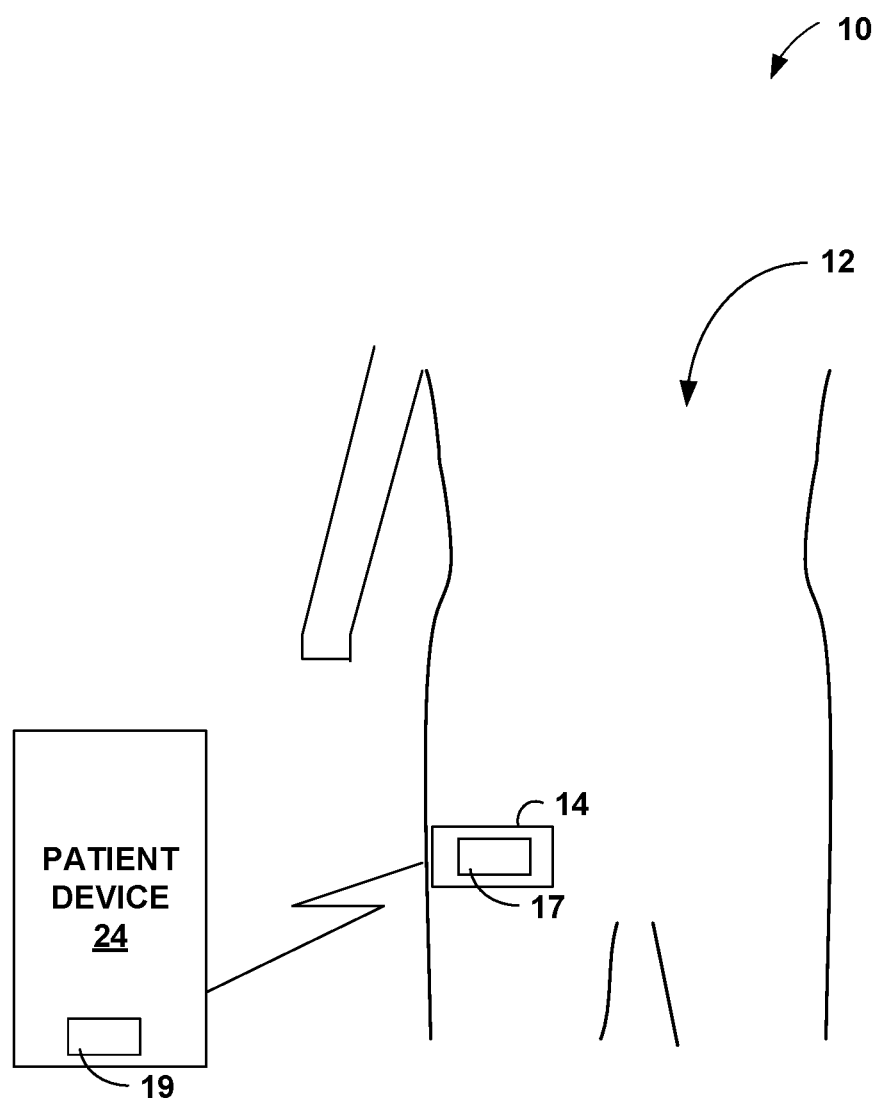
FIG. 1 is a block diagram illustrating an example medical system for detecting audible alerts, in accordance with one or more examples described in this disclosure.

FIG. 1 is a block diagram illustrating an example medical system for detecting audible alerts, in accordance with one or more examples described in this disclosure. FIG. 1 illustrates medical system 10 that includes medical device 14 and patient device 24. As shown in FIG. 1, patient 12 may wear or carry medical device 14. In some examples, if patient 12 is diabetic (e.g., Type 1 diabetic or Type 2 diabetic) such that the glucose level in patient 12 may be controlled with delivery of supplemental insulin, medical device 14 may comprise an insulin pump that delivers insulin into patient 12 and/or a glucose sensor that continuously or periodically samples the glucose level and rate of change of the glucose level over time.

In some examples, medical device 14 may be a relatively small device that patient 12 can place in different locations. For instance, patient 12 may clip medical device 14 to the waistband of pants worn by patient 12. In some examples, to be discreet, patient 12 may place medical device 14 in a pocket. In general, medical device 14 can be worn in various places, and patient 12 may place medical device 14 in a location based on the particular clothes patient 12 is wearing. In some examples, such as when medical device 14 is a patch pump, medical device 14 may include a cannula that is inserted under the skin of patient 12, such as near the stomach of patient 12 or in the arm of patient 12 (e.g., subcutaneous connection).

In some examples, patient 12 or a clinician may utilize patient device 24 to communicate with medical device 14. Patient device 24 may also be referred to throughout this disclosure as a "separate device"). Examples of patient device 24 include mobile devices (e.g., smartphones or tablet computers), laptop computers, wearable devices, and the like. In some examples, patient device 24 may be a special programmer or controller for medical device 14. Although FIG. 1 illustrates one patient device 24, in some examples, there may be a plurality of patient devices. For instance, system 10 may include a mobile device and a controller, each of which are examples of patient device 24. For ease of description only, the example techniques are described with respect to patient device 24, with the understanding that patient device 24 may be one or more patient devices.

Medical device 14 may output an audible alert upon determining an occurrence of an alert condition. Medical device 14 may also output, for display at a display of medical device 14 or for display at patient device 24, additional information regarding the alert condition. The audible alert may therefore act as an indication to patient 12 to view the display of medical device 14 or patient device 24 in order to view information regarding the alert condition.

In some examples, the alert condition may occur based on the glucose level of patient 12, such as when medical device 14 determines that the glucose level of patient 12 is too high or too low. In some examples, the alert condition may occur based on the status of medical device 14, such as when medical device 14 determines that it has a low battery and/or that it is time to replace all or part of medical device 14.

However, in some examples, medical device 14 may not include a speaker. Thus, medical device 14 may not be able to output an audible alert.

As such, in accordance with aspects of the present disclosure, when medical device 14 determines an occurrence of an alert condition, medical device 14 may transmit (e.g., wirelessly), to patient device 24, data indicative of the occurrence of the alert condition (e.g., a request to output an audible alert). For example, medical device 14 may use a short-range wireless connection, such as BLE, to wirelessly transmit a request to patient device 24. A short-range wireless connection, such as BLE, may have a limited communications range, such as a communications range of less than 100 meters, compared with other wireless connections, such as Wi-Fi. Using a short-range wireless connection may help ensure that patient 12 is able to hear an audible alert outputted by patient device 24, because a successful communication involves patient device 24 being within a predetermined range of medical device 14.

Further, using a short-range wireless connection facilitates secure communications. For example, it may be difficult to intercept communications in an undetected manner when a short-range wireless connection is used.

As such, in some examples, patient device 24 may be proximate to patient 12. For example, patient device 24 may be less than 10 feet away from patient 12.

The data indicative of the occurrence of the alert condition may include one or more data packets that include any suitable information that patient device 24 may process to determine that patient device 24 is to output an audible alert. In some examples, the one or more data packets may include, such as in the header of the one or more packets, data values that indicate an alert threshold has been exceeded. In some examples, the one or more data packets may include, such as in the header of the one or more packets, data values indicative of the one or more data packets being a request to output an audible alert.

In some examples, the data indicative of the occurrence of the alert condition may include one or more characteristics of a corresponding audible alert, such as the length (i.e., duration) of the audible alert, the frequency of the tone in the audible alert, the volume of the audible alert, whether the audible alert should be repeated, and the like. For example, responsive to obtaining the one or more characteristics, patient device 24 may output an audible alert according to the one or more characteristics. In some other examples, the data indicative of the occurrence of the alert condition may include information about the alert condition, and patient device 24 may use the information to determine one or more characteristics of a corresponding audible alert. For example, patient device 24 may maintain a set of associations between alert conditions and characteristics of corresponding audible alerts, and patient device 24 may access the set of associations to determine one or more characteristics of an audible alert corresponding to the occurrence of the alert condition.

Thus, responsive to receiving the data indicative of the occurrence of the alert condition, patient device 24 may output an audible alert via speaker 19 or any other suitable audio output device included in or coupled to patient device 24. For example, in response to receiving one or more data packets from medical device 14, patient device 24 may determine that one or more data values in the one or more data packets indicate that the one or more data packets correspond to a request to output an audible alert. In response to determining that the one or more data packets correspond to a request to output an audible alert, patient device 24 may output the audible alert via speaker 19 or any other suitable audio output device included in or coupled to patient device 24. Responsive to receiving the request to output the audible alert, patient device 24 may send, to medical device 14, a confirmation that patient device 24 has received the request.

However, for a variety of reasons, patient device 24 may not output an audible alert after medical device 14 transmits the data indicative of the occurrence of the alert condition. In some examples, if the silent mode on patient device 24 is enabled or if patient device 24 is set to a "do not disturb" mode, then patient device 24 may not output an audible alert. In some examples, an error may occur while patient device 24 is processing the data indicative of the occurrence of the alert condition. In some examples, even though patient device 24 is within wireless communication range of medical device 14, patient device 24 may be too far away from patient 12 such that the audible alert outputted by patient device 24 may not be loud enough to be clearly heard by patient 12.

Thus, after transmitting the data indicative of the occurrence of the alert condition to patient device 24, medical device 14 may determine whether an audible alert was outputted by patient device 24. To determine whether the audible alert was outputted by patient device 24, medical device 14 may use microphone 17 or any other suitable audio input device included in or coupled to medical device 14 to monitor for the audible alert. To use microphone 17 to monitor for the audible alert, medical device 14 may, after transmitting the data indicative of the occurrence of the alert condition, activate (e.g., turn on or place into an active mode) microphone 17 to capture audio. When microphone 17 is activated, microphone 17 may capture audio and may generate an audio signal, such as in the form of an electrical signal, that corresponds to the audio captured by microphone 17. To prevent microphone 17 from unnecessarily consuming power, medical device 14 may activate microphone 17 for a few seconds (e.g., fewer than five seconds) prior to deactivating (e.g., turning off) microphone 17.

Based on the audio signal generated by microphone 17, medical device 14 may determine whether at least a portion of the audio captured by microphone 17 includes an audible alert corresponding to the occurrence of the alert condition. For example, medical device 14 may process the audio signal to determine whether the audio captured by microphone 17 includes the audible alert that was requested by medical device 14 to be outputted by patient device 24. In some embodiments, medical device 14 may maintain an expected signal pattern for the audible alert in memory, and based on comparing the expected signal pattern with the audio signal obtained from microphone 17, medical device 14 may determine whether the audio captured by microphone 17 includes the audible alert. If medical device 14 determines that the expected signal pattern matches the audio signal obtained from microphone 17, medical device 14 may determine that the audible alert was outputted by patient device 24.

In some examples, determining whether patient device 24 has outputted the audible alert may involve determining whether the audio signal obtained from microphone 17 includes a tone at an expected frequency. This may be achieved based on applying a Goertzel filter to the audio signal to detect the presence of the tone. For example, medical device 14 may maintain (e.g., in memory) data indicative of the expected frequency of the tone (e.g., data resulting from application of a Goertzel filter to the tone), and medical device 14 may use a Goertzel filter to compare the expected frequency to a frequency of a tone in the audio signal obtained from microphone 17. Medical device 14 may determine that patient device 24 has outputted the audible alert when the frequency of the tone detected in the audio signal matches the expected frequency of the tone of the audible alert.

In some examples, different alert conditions may be associated with tones having different frequencies. For example, the frequency of a tone associated with a "low blood sugar" alert condition may differ from the frequency of a tone associated with a "malfunctioning device" alert condition. As such, medical device 14 may maintain an association of alert conditions with expected frequencies of tones. To determine whether the frequency of the tone detected in the audio signal matches an expected frequency, medical device 14 may determine the occurrence of the alert condition, determine the expected frequency of the tone associated with the audible alert corresponding to the alert condition, and compare the frequency of the tone in the audio signal to the expected frequency of tone associated with the audible alert.

In some examples, different levels of severity of the alert conditions may be associated with tones having different frequencies. For example the frequency of a tone associated with an alert condition at a higher level of severity may differ from the frequency of a tone associated with an alert condition at a lower level of severity. As such, medical device 14 may maintain an association of different levels of severity of alert conditions with expected frequencies of tones. To determine whether the frequency of the tone detected in the audio signal matches an expected frequency, medical device 14 may determine the occurrence of the alert condition, determine the level of severity of the alert condition, determine the expected frequency of the tone associated with the alert condition at the determined level of severity, and compare the frequency of the tone in the audio signal to the expected frequency of the tone associated with the determined level of severity of the alert condition.

In some examples, medical device 14 may use techniques other than applying a Goertzel filter to determine whether the frequency of the tone detected in the audio signal matches an expected frequency. For example, medical device 14 may apply one or more Fast Fourier Transforms to the audio signal to generate a representation of the audio signal in the frequency domain and may determine, based on the representation of the audio signal in the frequency domain, whether the frequency of the tone detected in the audio signal matches an expected frequency.

In some embodiments, in addition to determining that the frequency of the tone detected in the audio signal matches the expected frequency, medical device 14 may determine the signal strength of the detected tone. Because applying the Goertzel filter to the audio signal includes performing a Fourier transform on the audio signal, applying the Goertzel filter to the audio signal may provide the intensity of the audio signal in the frequency domain. Medical device 14 may therefore determine the signal strength of the tone based on the intensity of the detected tone in the frequency domain.

In some embodiments, in addition to determining the signal strength of the tone, medical device 14 may determine whether the signal strength of the tone exceeds a signal strength threshold. For example, this threshold may be determined based on averaging signal strengths of previously detected tones.

Based on determining that the frequency of the tone detected in the audio signal matches an expected frequency and that the signal strength of the tone exceeds the signal strength threshold, medical device 14 may determine that patient device 24 (or some other device that is separate from medical device 14) has outputted an alert that is audible to medical device 14. Because medical device 14 is typically located proximate to patient 12, it is generally safe to assume an alert that is audible to medical device 14 will also be audible to patient 12. Thus, medical device 14 may, upon determining that the audible alert is of sufficiently high signal strength (e.g. amplitude), determine that patient 12 was able to hear the audible alert outputted by patient device 24 and that the audible alert functionality of patient device 24 is operating correctly. However, if medical device 14 is unable to detect a tone having the expected frequency or if medical device 14 is unable to determine that the signal strength of a detected tone exceeds the signal strength threshold, medical device 14 may determine that patient device 24 failed to output an audible alert.

In some examples, medical device 14 may, upon determining that patient device 24 failed to output an audible alert, output a backup alert to notify patient 12 of the occurrence of the alert condition. For instance, if medical device 14 includes a speaker, medical device 14 may output an audible backup alert via the speaker. In another example, medical device 14 may produce haptic output to alert patient 12 to the occurrence of the alert condition.

In some examples, medical device 14 may, upon determining that patient device 24 failed to output an audible alert, determine whether to output a backup alert based on the type of the alert condition. For example, medical device 14 may output a backup alert for the occurrence of certain alert conditions but not for others. Thus, medical device 14 may, upon determining that patient device 24 failed to output an audible alert, determine whether the alert condition that occurred is an alert condition for which medical device 14 is to output a backup alert.

In some examples, medical device 14 may, upon determining that patient device 24 failed to output an audible alert, determine whether to output a backup alert based on the level of severity of the alert condition. For example, if alert conditions are categorized as having a high level of severity, a medium level of severity, or a low level of severity, medical device 14 may determine to output a backup alert only for the occurrence of alert conditions having a high level of severity. Thus, medical device 14 may, upon determining that patient device 24 failed to output an audible alert, determine whether the alert condition that occurred is categorized as having a level of severity for which medical device 14 is to output a backup alert.

In some examples, medical device 14 may, upon determining that patient device 24 failed to output an audible alert, cause patient device 24 to make another attempt to output an audible alert. For example, medical device 14 may send a request to patient device 24 to output the audible alert at an increased volume level and may perform any of the techniques described above to determine whether patient device 24 outputs an audible alert.

In some examples, medical device 14 and patient device 24 may periodically (e.g., once a day, once a week, once a month, etc.) perform a test to verify that patient device 24 is able to output audible alerts. For example, medical device 14 may wirelessly transmit to patient device 24 a request to play a test tone, which may be a high frequency tone. Patient device 24 may, responsive to receiving the request, output the test tone via speaker 19 or any other suitable audio output device included in or coupled to patient device 24. Medical device 14 may, upon sending the request, activate microphone 17 to capture audio and to generate the audio signal. Medical device 14 may determine, based on the audio signal and using techniques similar to any of those described above for detecting a tone, whether patient device 24 outputted the test tone. If medical device 14 determines that the test tone was outputted by patient device 24, medical device 14 may determine that the test was successful. If medical device 14 determines that the test tone was not outputted by patient device 24, medical device 14 may determine that the test was not successful.

Figure 2:
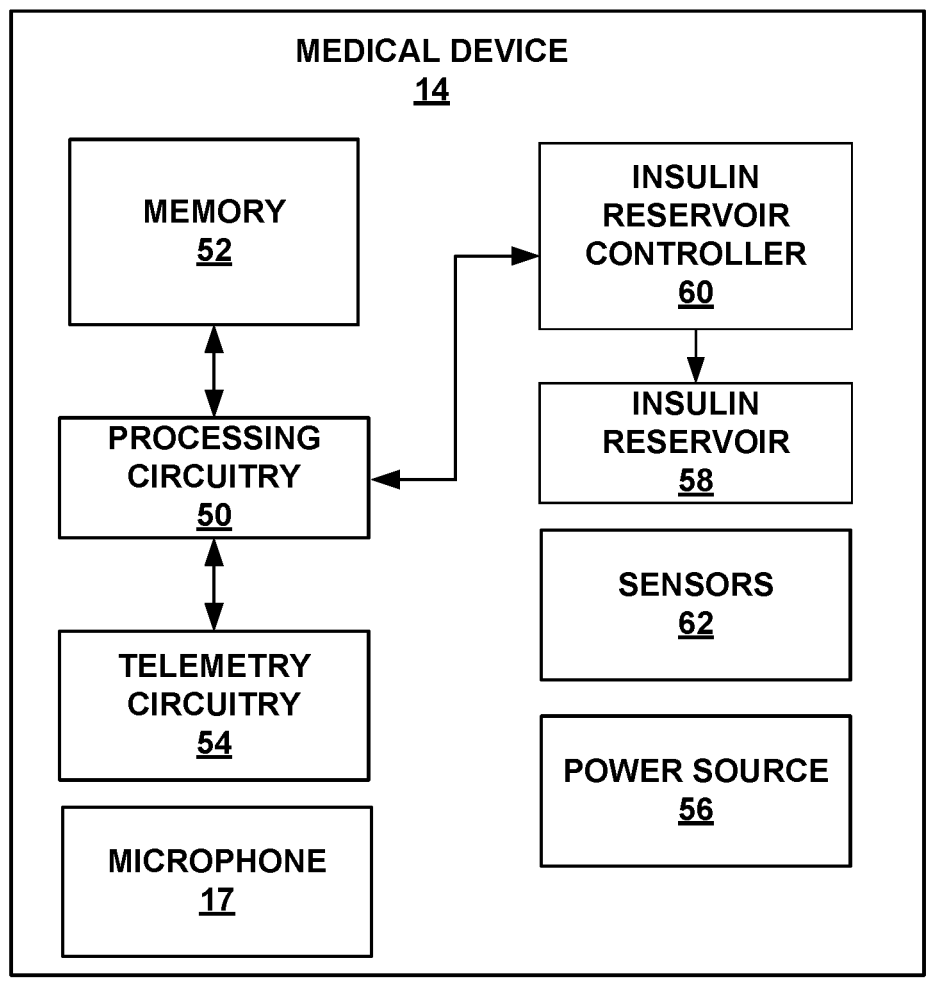
FIG. 2 is a block diagram illustrating an example of a medical device, in accordance with one or more examples described in this disclosure.

FIG. 2 is a block diagram illustrating an example of medical device 14, in accordance with one or more examples described in this disclosure. Examples of medical device 14 may include a glucose monitoring device, an insulin pump, and any other suitable medical device that is capable of being carried by, worn by, or attached to patient 12.

As illustrated, medical device 14 includes microphone 17, processing circuitry 50, memory 52, telemetry circuitry 54, power source 56, insulin reservoir 58, insulin reservoir controller 60, and one or more sensors 62. Medical device 14 may include more or fewer components than those illustrated in FIG. 2. For example, if medical device 14 is a glucose monitoring device, medical device 14 may not include insulin reservoir 58 and insulin reservoir controller 60.

Memory 52 may store program instructions that, when executed by processing circuitry 50, cause processing circuitry 50 to perform various functions (e.g., deliver insulin and/or measure a physiological characteristic of patient 12). Memory 52 may store user-specific configuration data, such as information indicative of insulin-on-board, basal rate, insulin limit, glucose sensor calibration factors, insulin sensitivity, and history of insulin delivery.

Memory 52 may include any volatile, non-volatile, fixed, removable, magnetic, optical, or electrical media, such as RAM, ROM, hard disk, removable magnetic disk, memory cards or sticks, NVRAM, EEPROM, flash memory, and the like. Processing circuitry 50 can include any one or more microprocessors, digital signal processors (DSPs), application specific integrated circuits (ASICs), field programmable gate arrays (FPGAs), or any other equivalent integrated or discrete logic circuitry, as well as any combinations of such components. The functions attributed to processing circuitry 50, as well as other processing circuitry described herein, may be embodied as hardware, firmware, software or any combination thereof.

In one or more examples, when medical device 20 is an insulin pump, processing circuitry 50 may utilize the user-specific configuration data stored in memory 52 to output instructions to insulin reservoir controller 60 to control when and how much insulin is outputted from insulin reservoir 58. For instance, insulin reservoir controller 60 may include a displacement mechanism that causes fixed amounts of insulin to be displaced from insulin reservoir 58 at a defined rate. Processing circuitry 50 may output commands that define the fixed amounts of insulin and the defined rate.

One or more sensors 62 include may include a glucose sensor configured to measure the glucose levels of patient 12. Microphone 17 may be any suitable audio capture device or audio input device. For example, microphone 17 may be implemented as circuitry configured to capture audio and to generate an audio signal, such as in the form of an electrical signal, that corresponds to the captured audio.

Telemetry circuitry 54 includes any suitable hardware, firmware, and/or software for communicating with another device, such as patient device 24. Telemetry circuitry 54 may send/receive communications with the aid of an antenna (not shown), which may be internal and/or external to medical device 14. Telemetry circuitry 54 may be configured to communicate with another computing device via wireless communication techniques or via a wired connection. Examples of local wireless communication techniques that may be employed to facilitate communication between medical device 14 and another computing device include RF communication according to IEEE 802.11, Bluetooth, or BLE specification sets, infrared communication (e.g., according to an IrDA standard), near field communication (NFC), or other standard or proprietary telemetry protocols. Telemetry circuitry 54 may also enable a connection with a carrier network. In this manner, other devices may be capable of communicating with medical device 14.

Power source 56 delivers operating power to the components of medical device 14. In some examples, power source 56 may include a battery, such as a rechargeable or non-rechargeable battery. A non-rechargeable battery may last for several days or possibly longer, while a rechargeable battery may be periodically charged with an external device, e.g., on a daily or weekly basis. Recharging of a rechargeable battery may be accomplished by using an alternating current (AC) outlet or through proximal inductive interaction between a charger device and an inductive charging coil within medical device 14. The inductive charging coil may be the same as or separate from the coil used for communication by telemetry circuitry 54.

Figure 3:
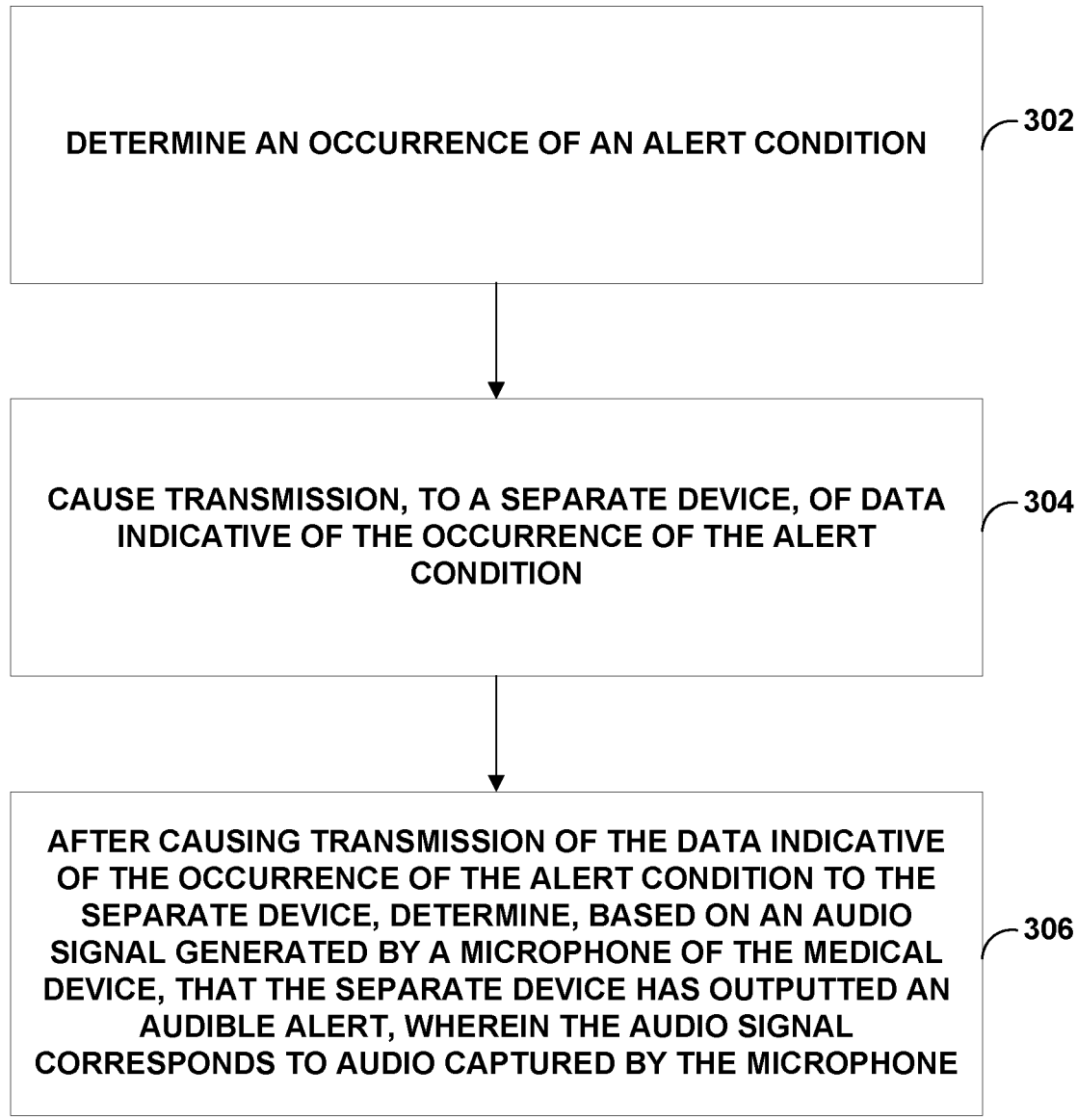
FIG. 3 is a flow diagram illustrating an example process for detecting audible alerts.

FIG. 3 is a flow diagram illustrating an example process for detecting audible alerts. Although FIG. 3 is described with respect to processing circuitry 50 of medical device 14 (FIG. 2), in other examples, different processing circuitry, alone or in combination with processing circuitry 50, may perform any part of the example process of FIG. 3.

As shown in FIG. 3, processing circuitry 50 of medical device 14 may determine an occurrence of an alert condition (302). An alert condition may be a condition associated with medical device 14 and/or patient 12 that warrants the attention of patient 12. Example alert conditions that relate to the condition of patient 12 include a hyperglycemic event and a hypoglycemic event. Example alert conditions that relate to the condition of medical device 14 include a system error event and a low battery event.

Processing circuitry 50 may, in addition to or as part of determining the occurrence of an alert condition, be configured to determine the level of severity of the alert condition. In some examples, processing circuitry 50 may categorize the level of severity of an alert condition as high severity, medium, severity, or low severity. In some examples, processing circuitry 50 may numerically quantify the level of severity on a numerical scale, such as from one to ten, where ten may correspond to the highest level of severity while one may correspond to the lowest level of severity.

Processing circuitry 50 may cause transmission of data indicative of the occurrence of the alert condition to a separate device (e.g., a device remote from medical device 14 such as patient device 24) (304).

Processing circuitry 50 may be configured to, upon determining the occurrence of an alert condition, transmit, via telemetry circuitry 54 to the separate device (e.g., patient device 24), data indicative of the occurrence of the alert condition (e.g., a request to output an audible alert). For example, telemetry circuitry 54 may establish a short-range wireless connection, such as a BLE connection, with patient device 24 to wirelessly transmit the data to patient device 24.

After causing transmission of the data indicative of the occurrence of the alert condition, processing circuitry 50 may determine, based on an audio signal generated by microphone 17, that the separate device (e.g., patient device 24) has outputted an audible alert (306). Processing circuitry 50 may be configured to, upon transmitting the data indicative of the occurrence of the alert condition, activate microphone 17 to listen for an audible alert. Microphone 17 may be configured to capture audio and to generate an audio signal, such as in the form of an electrical signal, that corresponds to the captured audio. Processing circuitry 50 may be configured to determine, based on the audio signal, whether the audio captured by microphone 17 includes an audible alert corresponding to the occurrence of the alert condition. If processing circuitry 50 determines that the audio captured by microphone 17 includes the audible alert, processing circuitry 50 may determine that the audible alert was outputted by patient device 24.

In some examples, processing circuitry 50 may be configured to determine, based on the audio signal, whether the audio captured by microphone 17 includes a tone at an expected frequency. If processing circuitry 50 determines that the audio captured by microphone 17 includes the tone at the expected frequency, processing circuitry 50 may determine that the audible alert was outputted by patient device 24.

In some examples, processing circuitry 50 may be configured to apply a Goertzel filter to the audio signal generated by microphone 17 to detect the presence of a tone having an expected frequency. For example, memory 52 may maintain an indication of the expected frequency of the tone, and processing circuitry 50 may be configured to determine, such as by applying a Goertzel filter to the audio signal, whether the audio signal includes a tone that matches the expected frequency.

In some examples, different alert conditions may be associated with different expected frequencies of alert tones, and memory 52 may be configured to maintain associations between alert conditions and expected frequencies of tones. Thus, to determine whether the audio signal includes a tone having an expected frequency, processing circuitry 50 may be configured to determine which alert condition occurred. Based on the associations between alert conditions and expected frequencies of tones, processing circuitry 50 may determine the expected frequency associated with the alert condition. Based on applying a Goertzel filter to the audio signal, processing circuitry 50 may determine whether the audio signal includes a tone that matches the expected frequency associated with the alert condition.

In some examples, different levels of severity for alert conditions may be associated with different expected frequencies of alert tones, and memory 52 may be configured to maintain associations between levels of severity and expected frequencies of tones. Thus, to determine whether the audio signal includes a tone having an expected frequency, processing circuitry 50 may be configured to determine which alert condition occurred as well as its level of severity. Based on the associations between levels of severity and expected frequencies of tones, processing circuitry 50 may determine the expected frequency associated with the level of severity of the alert condition. Based on applying a Goertzel filter to the audio signal, processing circuitry 50 may determine whether the audio signal includes a tone that matches the expected frequency associated with the level of severity of the alert condition.

Processing circuitry 50 may be configured to, upon determining that the frequency of the tone detected in the audio signal matches an expected frequency, determine the signal strength of the detected tone. For example, applying the Goertzel filter to the audio signal may yield the intensity of the audio signal in the frequency domain, and processing circuitry 50 may determine the signal strength of the tone based on the intensity of the detected tone in the frequency domain. Processing circuitry 50 may, for example, be configured to calculate the signal strength of the tone as a single byte of numerical value.

Processing circuitry 50 may be configured to, upon determining the signal strength of the tone, determine whether the signal strength of the tone exceeds a signal strength threshold. This may be achieved by comparing the signal strength of the tone, which may be the numerical value calculated above, to the signal strengths of other tones, such as numerical values representative of the signal strengths of sample tones pre-programmed into memory 52 or tones previously detected by medical device 14 and maintained in memory 52. For example, if processing circuitry 50 determines, based on comparing the signal strength of the tone to the signal strength of other tones, that the signal strength of the tone is at least 80% of the signal strengths of the other tones, processing circuitry 50 may determine that the signal strength of the tone exceeds the signal strength threshold.

Processing circuitry 50 may be configured to, upon determining that the frequency of the tone detected in the audio signal matches an expected frequency and that the signal strength of the tone exceeds the signal strength threshold, determine that a separate device (e.g., patient device 24) has outputted an alert that is audible to medical device 14. Based on determining that the alert is audible to medical device 14, processing circuitry 50 may determine that the audible alert functionality of the separate device is operating correctly.

If processing circuitry 50 is unable to detect a tone in the audio signal having a frequency that matches the expected frequency or if processing circuitry 50 is unable to determine that the signal strength of a detected tone exceeds the signal strength threshold, processing circuitry 50 may determine that the separate device failed to output an alert that was audible to medical device 14. In some examples, upon determining that the separate device failed to output an alert that was audible to medical device 14, processing circuitry 50 may cause medical device 14 to output a backup alert to notify patient 12 of the occurrence of the alert condition. In some examples, upon determining that the separate device failed to output an alert that was audible to medical device 14, processing circuitry 50 may determine whether to cause medical device 14 to output a backup alert based on the type of the alert condition. In some examples, upon determining that the separate device failed to output an alert that was audible to medical device 14, processing circuitry 50 may determine whether to cause medical device 14 to output a backup alert based on the level of severity of the alert condition.

This disclosure contains the following examples:

Example 1: A medical device includes a microphone configured to generate an audio signal indicative of audio captured by the microphone; one or more processors; and one or more processor-readable storage media storing instructions which, when executed by the one or more processors, cause performance of: determining an occurrence of an alert condition; transmitting, to a separate device, data indicative of the occurrence of the alert condition; and after transmitting the data indicative of the occurrence of the alert condition to the separate device, determining, based on the audio signal generated by the microphone, that the separate device has outputted an audible alert.

Example 2: The medical device of example 1, wherein determining, based on the audio signal generated by the microphone, whether the patient device has outputted the audible alert comprises: determining, based at least in part on applying a Goertzel filter on the audio signal, that a frequency of a tone in the audio captured by the microphone matches an expected frequency.

Example 3: The medical device of example 2, wherein determining, based at least in part on applying the Goertzel filter on the audio signal, that the frequency of the tone in the audio captured by the microphone matches the expected frequency comprises: determining the expected frequency associated with the alert condition from a plurality of expected frequencies associated with a plurality of alert conditions.

Example 4: The medical device of any of examples 2 and 3, wherein determining, based at least in part on applying the Goertzel filter on the audio signal, that the frequency of the tone in the audio captured by the microphone matches the expected frequency comprises: determining a level of severity associated with the alert condition; and determining the expected frequency associated with the level of severity from a plurality of expected frequencies associated with a plurality of levels of severity.

Example 5: The medical device of any of examples 2-4, wherein determining, based on the audio signal generated by the microphone, that the separate device has outputted the audible alert further comprises: responsive to determining that the frequency of the tone in the audio captured by the microphone matches the expected frequency, determining whether a signal strength of the tone exceeds a signal strength threshold; and responsive to determining that the frequency of the tone in the audio captured by the microphone matches the expected frequency and that the signal strength of the tone exceeds the signal strength threshold, determining that the patient device has outputted the audible alert.

Example 6: The medical device of any of examples 1-5, wherein the instructions which, when executed by the one or more processors, further cause performance of: determining a second occurrence of a second alert condition; transmitting, to the separate device, data indicative of the second occurrence of the second alert condition; after transmitting the data indicative of the second occurrence of the second alert condition to the separate device, determining, based on a second audio signal generated by the microphone, that the separate device has not outputted a second audible alert, wherein the second audio signal corresponds to second audio captured by the microphone; and responsive to determining that the separate device has not outputted the second audible alert, outputting a backup alert.

Example 7: The medical device of example 6, wherein outputting the backup alert comprises: determining a level of severity associated with the second alert condition; outputting the backup alert based at least in part on the level of severity associated with the second alert condition.

Example 8: The medical device of any of examples 1-7, wherein the instructions which, when executed by the one or more processors, further cause performance of: performing a test with the separate device, wherein performing the test comprises: transmitting, to the separate device, a request to play a high-frequency test tone, and after transmitting the request, determining that the separate device has outputted the high-frequency test tone.

Example 9: The medical device of any of examples 1-8, wherein transmitting, to the separate device, the data indicative of the occurrence of the alert condition comprises: wirelessly transmitting, to the separate device, a request to output the audible alert.

Example 10: A method includes determining, by one or more processors of a medical device, an occurrence of an alert condition; causing transmission, by the one or more processors and to a separate device, of data indicative of the occurrence of the alert condition; and after causing transmission of the data indicative of the occurrence of the alert condition to the separate device, determining, by the one or more processors and based on an audio signal generated by a microphone of the medical device, that the separate device has outputted an audible alert, wherein the audio signal corresponds to audio captured by the microphone.

Example 11: The method of example 10, wherein determining, based on the audio signal generated by the microphone, that the separate device has outputted the audible alert comprises: determining, by the one or more processors and based at least in part on applying a Goertzel filter on the audio signal, that a frequency of a tone in the audio captured by the microphone matches an expected frequency.

Example 12: The method of example 11, wherein determining, based at least in part on applying the Goertzel filter on the audio signal, that the frequency of the tone in the audio captured by the microphone matches the expected frequency comprises: determining, by the one or more processors, the expected frequency associated with the alert condition from a plurality of expected frequencies associated with a plurality of alert conditions.

Example 13: The method of any of examples 11 and 12, wherein determining, based at least in part on applying the Goertzel filter on the audio signal, that the frequency of the tone in the audio captured by the microphone matches the expected frequency comprises: determining, by the one or more processors, a level of severity associated with the alert condition; and determining, by the one or more processors, the expected frequency associated with the level of severity from a plurality of expected frequencies associated with a plurality of levels of severity.

Example 14: The method of any of examples 11-13, wherein determining, based on the audio signal generated by the microphone, that the separate device has outputted the audible alert further comprises: responsive to determining that the frequency of the tone in the audio captured by the microphone matches the expected frequency, determining, by the one or more processors, whether a signal strength of the tone exceeds a signal strength threshold; and responsive to determining that the frequency of the tone in the audio captured by the microphone matches the expected frequency and that the signal strength of the tone exceeds the signal strength threshold, determining, by the one or more processors, that the separate device has outputted the audible alert.

Example 15: The method of any of examples 10-14, further includes determining a second occurrence of a second alert condition; causing transmission, to the separate device, of data indicative of the second occurrence of the second alert condition; after causing transmission of the data indicative of the second occurrence of the second alert condition to the separate device, determining, based on a second audio signal generated by the microphone, that the separate device has not outputted a second audible alert, wherein the second audio signal corresponds to second audio captured by the microphone; and responsive to determining that the separate device has not outputted the second audible alert, causing output of a backup alert.

Example 16: The method of example 15, wherein causing output of the backup alert comprises: determining a level of severity associated with the second alert condition; causing output of the backup alert based at least in part on the level of severity associated with the second alert condition.

Example 17: The method of any of examples 10-16, further includes performing, by the one or more processors, a test with the separate device, wherein performing the test comprises: causing transmission, by the one or more processors and to the separate device, a request to play a high-frequency test tone, and determining, by the one or more processors, that the separate device has outputted the high-frequency test tone.

Example 18: The method of any of examples 10-17, wherein causing transmission, to the separate device, of the data indicative of the occurrence of the alert condition comprises: causing wireless transmission, by the one or more processors and to the separate device, of a request to output the audible alert.

Example 19: One or more non-transitory processor-readable storage media storing instructions which, when executed by one or more processors of a medical device, cause performance of: determining an occurrence of an alert condition; transmitting, to a separate device, data indicative of the occurrence of the alert condition; and after transmitting the data indicative of the occurrence of the alert condition to the separate device, determining, based on an audio signal generated by a microphone, that the separate device has outputted an audible alert, wherein the audio signal corresponds to audio captured by the microphone.

Example 20: The one or more non-transitory processor-readable storage media of example 19, wherein determining, based on the audio signal generated by the microphone, that the patient device has outputted the audible alert comprises: determining, based at least in part on applying a Goertzel filter on the audio signal, that a frequency of a tone in the audio captured by the microphone matches an expected frequency.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including processing circuitry 50 of medical device 14, one or more processors of patient device 24, or some combination thereof. The one or more processors may be one or more integrated circuits (ICs), and/or discrete electrical circuitry, residing in various locations in the example systems described in this disclosure.

The one or more processors or processing circuitry utilized for example techniques described in this disclosure may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. The processors or processing circuitry may include arithmetic logic units (ALUs), elementary function units (EFUs), digital circuits, analog circuits, and/or programmable cores, formed from programmable circuits. In examples where the operations of the processors or processing circuitry are performed using software executed by the programmable circuits, memory accessible by the processors or processing circuitry may store the object code of the software that the processors or processing circuitry receive and execute.

Various aspects of the disclosure have been described. These and other aspects are within the scope of the following claims.

What is claimed is:

1. A medical device comprising:
a microphone configured to generate an audio signal indicative of audio captured by the microphone;
one or more processors; and
one or more processor-readable storage media storing instructions which, when executed by the one or more processors, cause performance of:
determining an occurrence of an alert condition;
transmitting, to a separate device and via a short-range wireless communication channel, data indicative of the occurrence of the alert condition, wherein the separate device is physically separate from the medical device;
after transmitting the data indicative of the occurrence of the alert condition to the separate device, determining, based on the audio signal generated by the microphone, whether the separate device has outputted an audible alert indicative of the alert condition; and
responsive to determining that the separate device has not outputted the audible alert, causing performance of one or more remedial actions until the microphone generates a different audio signal indicative of the separate device outputting the audible alert indicative of the alert condition.

2. The medical device of claim 1, wherein determining, based on the audio signal generated by the microphone, whether the separate device has outputted the audible alert comprises:
determining, based at least in part on applying a Goertzel filter on the audio signal, that a frequency of a tone in the audio signal captured by the microphone matches an expected frequency.

3. The medical device of claim 2, wherein determining, based at least in part on applying the Goertzel filter on the audio signal, that the frequency of the tone in the audio signal captured by the microphone matches the expected frequency comprises:
determining the expected frequency associated with the alert condition from a plurality of expected frequencies associated with a plurality of alert conditions.

4. The medical device of claim 2, wherein determining, based at least in part on applying the Goertzel filter on the audio signal, that the frequency of the tone in the audio signal captured by the microphone matches the expected frequency comprises:
determining a level of severity associated with the alert condition; and
determining the expected frequency associated with the level of severity from a plurality of expected frequencies associated with a plurality of levels of severity.

5. The medical device of claim 2, wherein determining, based on the audio signal generated by the microphone, whether the separate device has outputted the audible alert further comprises:
responsive to determining that the frequency of the tone in the audio signal captured by the microphone matches the expected frequency, determining whether a signal strength of the tone exceeds a signal strength threshold; and
responsive to determining that the frequency of the tone in the audio signal captured by the microphone matches the expected frequency and that the signal strength of the tone exceeds the signal strength threshold, determining that the separate device has outputted the audible alert.

6. The medical device of claim 1, wherein the one or more remedial actions comprise outputting a backup alert, wherein outputting the backup alert comprises:
determining a level of severity associated with a second alert condition; and
outputting the backup alert based at least in part on the level of severity associated with the second alert condition.

7. The medical device of claim 1, wherein the instructions which, when executed by the one or more processors, further cause performance of:
performing a test with the separate device, wherein performing the test comprises:
transmitting, to the separate device, a request to play a high-frequency test tone, and
after transmitting the request, determining that the separate device has outputted the high-frequency test tone.

8. The medical device of claim 1, wherein transmitting, to the separate device, the data indicative of the occurrence of the alert condition comprises:
wirelessly transmitting, to the separate device, a request to output the audible alert.

9. A method comprising:
determining, by one or more processors of a medical device, an occurrence of an alert condition;
causing transmission, by the one or more processors and to a separate device via a short-range wireless communication channel, of data indicative of the occurrence of the alert condition, wherein the separate device is physically separate from the medical device;
after causing transmission of the data indicative of the occurrence of the alert condition to the separate device, determining, by the one or more processors and based on an audio signal generated by a microphone of the medical device, whether the separate device has outputted an audible alert indicative of the alert condition, wherein the audio signal corresponds to audio captured by the microphone; and
responsive to determining that the separate device has not outputted the audible alert, causing, by the one or more processors, performance of one or more remedial actions until the microphone generates a different audio signal indicative of the separate device outputting the audible alert indicative of the alert condition.

10. The method of claim 9, wherein determining, based on the audio signal generated by the microphone, whether the separate device has outputted the audible alert comprises:
determining, by the one or more processors and based at least in part on applying a Goertzel filter on the audio signal, that a frequency of a tone in the audio signal captured by the microphone matches an expected frequency.

11. The method of claim 10, wherein determining, based at least in part on applying the Goertzel filter on the audio signal, that the frequency of the tone in the audio signal captured by the microphone matches the expected frequency comprises:
determining, by the one or more processors, the expected frequency associated with the alert condition from a plurality of expected frequencies associated with a plurality of alert conditions.

12. The method of claim 10, wherein determining, based at least in part on applying the Goertzel filter on the audio signal, that the frequency of the tone in the audio signal captured by the microphone matches the expected frequency comprises:

determining, by the one or more processors, a level of severity associated with the alert condition; and determining, by the one or more processors, the expected frequency associated with the level of severity from a plurality of expected frequencies associated with a plurality of levels of severity.

13. The method of claim 10, wherein determining, based on the audio signal generated by the microphone, whether the separate device has outputted the audible alert further comprises:

responsive to determining that the frequency of the tone in the audio signal captured by the microphone matches the expected frequency, determining, by the one or more processors, whether a signal strength of the tone exceeds a signal strength threshold; and responsive to determining that the frequency of the tone in the audio signal captured by the microphone matches the expected frequency and that the signal strength of the tone exceeds the signal strength threshold, determining, by the one or more processors, that the separate device has outputted the audible alert.

14. The method of claim 9, further comprising outputting a backup alert, and wherein causing outputting of the backup alert comprises: determining a level of severity associated with a second alert condition; and causing output of the backup alert based at least in part on the level of severity associated with the second alert condition.

15. The method of claim 9, further comprising:

performing, by the one or more processors, a test with the separate device, wherein performing the test comprises:

causing transmission, by the one or more processors and to the separate device, a request to play a high-frequency test tone, and determining, by the one or more processors, that the separate device has outputted the high-frequency test tone.

16. The method of claim 9, wherein causing transmission, to the separate device, of the data indicative of the occurrence of the alert condition comprises:

causing wireless transmission, by the one or more processors and to the separate device, of a request to output the audible alert.

17. One or more non-transitory processor-readable storage media storing instructions which, when executed by one or more processors of a medical device, cause performance of:

determining an occurrence of an alert condition;

transmitting, to a separate device via a short-range wireless communication channel, data indicative of the occurrence of the alert condition, wherein the separate device is physically separate from the medical device;

after transmitting the data indicative of the occurrence of the alert condition to the separate device, determining, based on an audio signal generated by a microphone, whether the separate device has outputted an audible alert indicative of the alert condition, wherein the audio signal corresponds to audio captured by the microphone; and responsive to determining that the separate device has not outputted the audible alert, causing performance of one or more remedial actions until the microphone generates a different audio signal indicative of the separate device outputting the audible alert indicative of the alert condition.

18. The one or more non-transitory processor-readable storage media of claim 17, wherein determining, based on the audio signal generated by the microphone, whether the separate device has outputted the audible alert comprises:

determining, based at least in part on applying a Goertzel filter on the audio signal, that a frequency of a tone in the audio signal captured by the microphone matches an expected frequency.

* * * * *